US010799540B2

(12) United States Patent
Zou et al.

(10) Patent No.: US 10,799,540 B2
(45) Date of Patent: Oct. 13, 2020

(54) FAECALIBACTERIUM LONGUM AND APPLICATION THEREOF

(71) Applicant: BGI SHENZHEN, Shenzhen (CN)

(72) Inventors: Yuanqiang Zou, Shenzhen (CN); Wenbin Xue, Shenzhen (CN); Liang Xiao, Shenzhen (CN); Chuan Liu, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 0 days.

(21) Appl. No.: 16/082,769

(22) PCT Filed: Sep. 6, 2016

(86) PCT No.: PCT/CN2016/098246
§ 371 (c)(1),
(2) Date: Apr. 23, 2019

(87) PCT Pub. No.: WO2018/045492
PCT Pub. Date: Mar. 15, 2018

(65) Prior Publication Data
US 2019/0240264 A1    Aug. 8, 2019

(51) Int. Cl.
| | | |
|---|---|---|
| *A61K 35/74* | (2015.01) | |
| *C12N 1/20* | (2006.01) | |
| *A61K 35/741* | (2015.01) | |
| *A23L 33/135* | (2016.01) | |
| *A61P 3/08* | (2006.01) | |
| *A61P 3/10* | (2006.01) | |
| *A61K 35/20* | (2006.01) | |
| *C12R 1/01* | (2006.01) | |

(52) U.S. Cl.
CPC .......... *A61K 35/741* (2013.01); *A23L 33/135* (2016.08); *A61K 35/20* (2013.01); *A61K 35/74* (2013.01); *A61P 3/08* (2018.01); *A61P 3/10* (2018.01); *C12N 1/20* (2013.01); *C12R 1/01* (2013.01); *A23V 2002/00* (2013.01)

(58) Field of Classification Search
CPC ...... A61K 35/741; A61K 35/74; A61K 35/20; A61P 3/08; A61P 3/10; C12R 1/01; C12N 1/20; A23L 33/135; A23V 2002/00
See application file for complete search history.

(56) References Cited

FOREIGN PATENT DOCUMENTS

| CN | 10-4363769 A | 2/2015 |
|---|---|---|
| CN | 10-4415060 A | 3/2015 |
| CN | 10-4432001 A | 3/2015 |
| CN | 10-5228635 A | 1/2016 |

OTHER PUBLICATIONS

Mayo Clinic Staff. Strategies to Prevent Heart Disease. Mayo Clinic. Retrieved from: https://www.mayoclinic.org/diseases-conditions/heart-disease/in-depth/heart-disease-prevention/art-20046502 (Year: 2019).*
Harvard Health Publishing: Harvard Medical School. Publish 2009, updated 2019. Why People Become Overweight. https://www.health.harvard.edu/staying-healthy/why-people-become-overweight (Year: 2009).*
Dowshen, S. 2018. Can Diabetes Be Prevented?. Retrieved from: https://kidshealth.org/en/parents/prevention.html (Year: 2018).*
Watawana, M.I. et al. 2015. Health, Wellness, and Safety Aspects of the Consumption of Kombucha. Journal of Chemistry. Article ID: 591869. 11 pages. (Year: 2015).*
Barcenilla et al., "Phylogenetic Relationships of Butyrate-Producing Bacteria from the Human Gut," *Applied and Environmental Microbiology* 66(4):1654-1661 (Apr. 2000).

* cited by examiner

*Primary Examiner* — Michelle F. Paguio Frising
*Assistant Examiner* — Kasandra S Hunter
(74) *Attorney, Agent, or Firm* — Westman, Champlin & Koehler, P.A.; Z. Peter Sawicki; Amanda M. Prose

(57) ABSTRACT

Provided are *Faecalibacterium longum* and an application thereof, specifically, use of *Faecalibacterium longum* in treating and preventing diabetes and related diseases thereof. Also provided are a composition for treating and preventing diabetes and related diseases thereof, comprising compositions of drugs, drinks, food, or animal feed, and a method for reducing weight, fasting plasma glucose and/or blood lipid, and improving glucose tolerance.

20 Claims, 3 Drawing Sheets
Specification includes a Sequence Listing.

FAECALIBACTERIUM LONGUM AND APPLICATION THEREOF

CROSS-REFERENCE TO RELATED APPLICATION

This Application is a Section 371 National Stage Application of International Application No. PCT/CN2016/098246, filed Sep. 6, 2016, and published as WO 2018/045492 A1 on Mar. 15, 2018, not in English, the content of which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 140214_402US_SEQUENCE_LISTING.txt. The text file is 2.4 KB, was created on Sep. 6, 2018, and is being submitted electronically via EFS-web.

TECHNICAL FIELD

The present invention relates to the field of microbiology, in particular, the present invention relates to a use of *Faecalibacterium longum* in the treatment and prevention of diabetes as well as the associated diseases thereof, and also relates to a composition comprising *Faecalibacterium longum* and the use thereof.

BACKGROUND

A large number of symbiotic microorganisms are colonized in the human intestine. These symbiotic microbial populations constitute the "second organ" of the human body. They not only participate in the digestion and absorption of nutrients with hosts in synergy, but also play an important role in the maintenance of human health. In terms of the number of cells, the number of all cells of intestinal microbes is 10 times larger than that of human cells. These large microbial populations mainly have two species: Firmicutes and Bacteroidetes. More and more studies have shown that the composition and diversity of intestinal microbes are closely related to the occurrence of multiple diseases, such as obesity, diabetes, irritable bowel syndrome, ulcerative enteritis, colon cancer, fatty liver and the like. Due to the influence of environment, diet, drugs, etc., the balance of intestinal microbes in the original state of health is broken, leading to intestinal dysfunction, which in turn induces the occurrence of the above diseases.

In recent years, with the improvement of people's daily life, the dietary structure is gradually unbalanced, and the incidence of metabolic diseases such as obesity and diabetes has increased rapidly. According to the statistics of World Health Organization, there are approximately 422 million people with diabetes worldwide in 2014. By 2012, the number of deaths caused by diabetes has reached 1.5 million. Therefore, diabetes has become a major public health issue. Diabetes is a disease with abnormally high blood sugar caused by many factors, mainly due to metabolic disorders caused by insufficient insulin secretion or defects in insulin function. Common risk factors for diabetes are genetic factors, environmental factors and bad living habits. The occurrence of diabetes is accompanied by many complications, such as coronary heart disease, hypertension, myocardial infarction, stroke, senile dementia, Parkinson's disease, kidney disease, retinopathy, etc., which seriously reduce the life quality of patients. Type 2 diabetes is a type of non-insulin-dependent diabetes, which accounts for 90% of all patients with diabetes. Numerous studies have shown that the pathogenesis of type 2 diabetes is closely related to the disorder of the intestinal flora. The intestinal flora is closely related to the regulation of energy balance and inflammatory reaction among the hosts. The pathogenesis of type 2 diabetes is mainly caused by insulin resistance and low levels of inflammatory response.

Currently, the hypoglycemic drugs used for the treatment of diabetes include sulfonylureas, $\alpha$-glucosidase inhibitors and biguanides, wherein sulfonylureas are mainly used to promote insulin secretion, but can cause severe liver and kidney damage, and it is not suitable to take for allergic constitution; $\alpha$-glucosidase inhibitors mainly inhibit the hydrolysis of carbohydrates by inhibiting the activity of $\alpha$-amylase and intestinal $\alpha$-glucosidase, thereby reducing the postprandial blood glucose, but easily cause adverse reactions, such as abdominal distension and diarrhea; and biguanides can reduce blood glucose by regulating blood sugar transport, such as delaying sugar absorption, promoting glucose decomposition, inhibiting liver glucose production, and increasing the level of glucose transfer protein. Biguanides can also cause some side effects, such as gastrointestinal discomfort, diarrhea, vomiting, and rash. Inactivation is easy to be occurred after long-term use.

Therefore, there is an urgent need in the art to develop a new, non-toxic and side-effect drug for the treatment and prevention of diabetes and associated diseases.

SUMMARY OF INVENTION

Another object of the present invention is to provide a use of the *Faecalibacterium longum* for the treatment and prevention of diabetes and associated diseases.

Another object of the present invention is to provide an effective pharmaceutical, beverage, food composition, or animal feed composition without toxic and side-effect for the treatment and prevention of diabetes and associated diseases.

Another object of the present invention is to provide a method for reducing body weight, fasting blood glucose and/or blood lipid and an application thereof.

Another object of the present invention is to provide a method for improving glucose tolerance and an application thereof.

In the first aspect of the present invention, a *Faecalibacterium longum* is provided, which is *Faecalibacterium longum*.

In another preferred embodiment, the sequence of 16s rDNA of *Faecalibacterium longum* is as set forth by SEQ ID NO.: 1.

In another preferred embodiment, the *Faecalibacterium longum* is *Faecalibacterium longum* CM04-06 with a deposit number of CGMCC 1.5208.

In the second aspect of the present invention, a composition is provided, which comprises: (a) a safe and effective amount of *Faecalibacterium longum* of claim 1 and/or metabolites thereof; and (b) a food acceptable carrier or a pharmaceutically acceptable carrier.

In another preferred embodiment, the composition further comprises a milk growth factor.

In another preferred embodiment, the composition is selected from the group consisting of: a food composition, a health care composition, a pharmaceutical composition, a beverage composition, a feed composition, and a combination thereof.

In another preferred embodiment, the composition is an oral preparation.

In another preferred embodiment, the composition is a liquid preparation, a solid preparation, or a semi-solid preparation.

In another preferred embodiment, the dosage form of the composition is selected from the group consisting of a powder, pulvis, tablet, sugar coating agent, capsule, granule, suspension, solution, syrup, drop, and sublingual tablet.

In another preferred embodiment, the food composition comprises an emulsion product, a solution product, a powder product, or a suspension product.

In another preferred embodiment, the food composition comprises a dairy product, milk powder, or emulsion.

In another preferred embodiment, the liquid preparation is selected from the group consisting of a solution product or a suspension product.

In another preferred embodiment, the composition comprises $1 \times 10$-$1 \times 10^{10}$ cfu/mL or cfu/g of *Faecalibacterium longum* CM04-06, preferably $1 \times 10^{4}$-$1 \times 10^{10}$ cfu/mL or cfu/g of *Faecalibacterium longum* CM04-06, based on the total volume or total weight of the composition.

In another preferred embodiment, the composition comprises from 0.0001 to 99 wt %, preferably from 0.1 to 90 wt % of the *Faecalibacterium longum* and/or the metabolites thereof, based on the total weight of the composition.

In another preferred embodiment, the composition is in a unit dosage form (one tablet, one capsule or one vial) and the mass of the composition in each unit dosage form is from 0.05 to 5 g, preferably from 0.1 to 1 g.

In another preferred embodiment, the composition further comprises other probiotic(s) and/or prebiotic(s).

In another preferred embodiment, the probiotic is selected from the group consisting of *Lactobacillus*, bifidobacteria, *Lactobacillus acidophilus*, and a combination thereof.

In another preferred embodiment, the prebiotic is selected from the group consisting of fructooligosaccharide (FOS), galactooligosaccharide (GOS), xylooligosaccharide (XOS), lactosucrose (LACT), soybean oligosaccharides (SOS), Inulin, and a combination thereof.

In the third aspect of the present invention, a use of a *Faecalibacterium longum* according to the first aspect of the present invention, or a composition according to the second aspect of the present invention is provided, for the preparation of a medicament or preparation, which is used for one or more of the applications selected from the group consisting of: (a) prevention and/or treatment of obesity; (b) reduction of blood lipids; (c) prevention or treatment of cardiovascular disease; and/or (d) prevention and/or treatment of diabetes.

In another preferred embodiment, the preparation comprises a microecological preparation.

In the fourth aspect of the present invention, a use of a *Faecalibacterium longum* according to the first aspect of the present invention, or a composition according to the second aspect of the present invention is provided, for the preparation of a medicament or preparation, which is used for one or more of the applications selected from the group consisting of:

(i) inhibition of the weight gain in mammals;
(ii) reduction of blood lipid level in mammals;
(iii) increase of high density lipoprotein (HDL-C) level in mammals;

(iv) reduction of low-density lipoprotein (LDL-C) level in mammals;
(v) reduction of blood glucose level in mammals;
(vi) increase of glucose tolerance in mammals.

In another preferred embodiment, the mammal comprises human, a rodent (such as a rat, or a mouse).

In another preferred embodiment, the reduction of blood lipid level in mammals comprises the reduction of total cholesterol (TC) level and/or triglyceride level.

In another preferred embodiment, the reduction of blood glucose level in mammals comprises the reduction of fasting blood glucose level.

In the fifth aspect of the present invention, a method for preparing the composition according to the second aspect of the present invention is provided, comprising a step of:

mixing the *Faecalibacterium longum* according to the first aspect of the present invention and/or the metabolites thereof with a food acceptable carrier or a pharmaceutically acceptable carrier, thereby forming the composition according to the second aspect of the present invention.

In another preferred embodiment, the method further comprises the step of mixing with a growth factor.

In another preferred embodiment, the growth factor is a milk growth factor.

In another preferred embodiment, the growth factor is selected from the group consisting of vitamins, purines, pyrimidines, and a combination thereof.

In another preferred embodiment, the composition is an oral preparation.

In the sixth aspect of the present invention, a production method is provided, comprising the following steps:

(a) cultivating the *Faecalibacterium longum* according to the first aspect of the present invention under a condition suitable for cultivation, thereby obtaining a culture product;

(b) optionally, isolating *Faecalibacterium longum* thalluses and/or metabolites thereof from the culture product; and (c) optionally, mixing the obtained *Faecalibacterium longum* thalluses and/or the metabolites thereof isolated from the previous step with a food acceptable carrier or pharmaceutically acceptable carrier, thereby obtaining a composition.

In another preferred embodiment, prior to step (c), the method further comprises the step of mixing the isolated and obtained *Faecalibacterium longum* thalluses and/or the metabolites thereof with a growth factor.

In another preferred embodiment, the growth factor is a milk growth factor.

In another preferred embodiment, the growth factor is selected from the group consisting of vitamins, purines, pyrimidines, and a combination thereof.

In the seventh aspect of the present invention, a method for reducing weight, fasting blood sugar and/or blood lipid is provided, comprising administering the *Faecalibacterium longum* according to the first aspect of the present invention and/or metabolites thereof or the composition according to the second aspect of the present invention to a subject.

In another preferred embodiment, the administration comprises oral administration.

In another preferred embodiment, dosage for administering is 0.01-5 g/50 kg body weight/day, preferably is 0.1-2 g/50 kg body weight/day.

In another preferred embodiment, the subject comprises a mammal, such as a human.

In the eighth aspect of the present invention, a method for improving glucose tolerance is provided, comprising administering the *Faecalibacterium longum* according to the first aspect of the present invention and/or metabolites thereof or the composition according to the second aspect of the present invention to a subject.

In another preferred embodiment, the administration comprises oral administration.

In another preferred embodiment, dosage for administering is 0.01-5 g/50 kg body weight/day, preferably is 0.1-2 g/50 kg body weight/day.

In another preferred embodiment, the subject comprises a mammal, such as a human.

It should be understood that, within the scope of the present invention, each technical feature of the present invention described above and in the following (as examples) may be combined with each other to form a new or preferred technical solution, which is not listed here due to space limitations.

DETAILED DESCRIPTION

Figure 1:
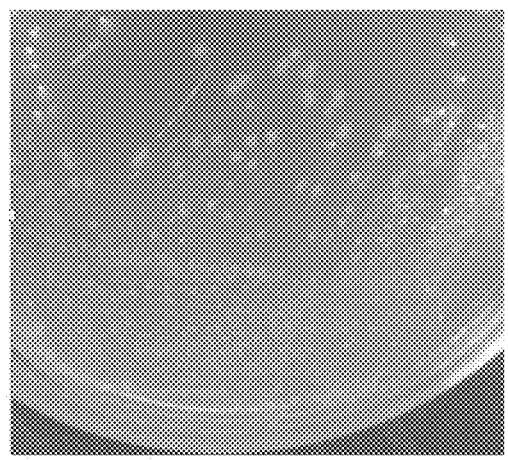
FIG. 1 shows an image of the colonies of *Faecalibacterium longum* cultured for 3 days.

Upon extensive and intensive studies and experiments, the inventors have unexpectedly found that *Faecalibacterium longum* has the effect of preventing and treating diabetes and the diabetes-associated diseases, such as cardiovascular diseases and obesity diseases. After being fed to the experimental subjects, the active composition containing *Faecalibacterium longum* is found to possess the ability to inhibit weight gain, lower the blood lipid, lower the fasting blood glucose, improve glucose tolerance and effectively alleviate diabetes, cardiovascular and obesity and other diseases. On this basis, the inventors completed the present invention.

As used herein, the term "comprising" means that various ingredients may be together employed in a mixture or composition of the present invention. Thus, the terms "consisting essentially of" and "consisting of" are encompassed in the term "comprising".

As used herein, the terms "growth factor" and "milk growth factor" can be used interchangeably and include vitamins, purines, pyrimidines, and nutrients of a combination thereof.

Wherein, the vitamins include, but are not limited to: vitamin C, vitamin E, vitamin A, vitamin A precursor, vitamin $B_6$, vitamin $D_3$, vitamin K, folic acid, and a combination thereof;

the purines include, but are not limited to, a purine nucleoside, wherein the purine nucleoside comprises a 5'-phosphate of a purine nucleoside, and the 5'-phosphate of the purine nucleoside is selected from the group consisting of: inosinic acid (inosine-5'-phosphate; IMP), guanylic acid (guanosine-5'-phosphate; GMP), xanthine nucleotide (xanthosine-5'-phosphate; XMP), adenylic acid (adenosine-5'-phosphate; AMP), and a combination thereof;

the pyrimidines include all substances containing a pyrimidine structure.

Faecalibacterium longum and Use Thereof

As used herein, the terms "*Faecalibacterium*" and "*Faecalibacterium longum*" can be used interchangeably. In a preferred embodiment, the strain is *Faecalibacterium longum* CM04-06 with a deposit number of CGMCC 1.5208, isolated from human faeces. Physiological characteristics of *Faecalibacterium longum* are shown as follows: the *Faecalibacterium longum* is cultured in an anaerobic environment at 37° C. for 2-3 days. The colonies present a yellowish white, with a higher water content, a little sticky, nearly round, opaque, flat with a bulge in the middle, and the diameter of the colony is about 2-3 mm; after the Gram staining, the microscopic observation shows that CM04-06 are non-spore and non-flagella, Gram-negative bacteria with long rod-shape, the diameter of the bacteria is about 1 um, the length is 4-10 um; and the oxidase and catalase reactions of the *Faecalibacterium longum* of the present invention are both negative, the growth temperature ranges from 30 to 45° C., the pH ranges from 4.0 to 9.0, and the optimum temperature and pH are 37° C. and pH 7.0, and it can tolerate 3% of NaCl. It can ferment several carbohydrates, including mannose, raffinose, and trehalose to produce formic acid, acetic acid, butyric acid and lactic acid, in addition, extracellular polysaccharides can also be produced by fermentation.

The present invention provides the use of *Faecalibacterium longum* in the treatment and prevention of diabetes and related diseases such as cardiovascular diseases and obesity diseases. The subject ingests a high-fat diet, the *Faecalibacterium longum* CM04-06 strain has one or more uses selected from the group consisting of: (i) inhibiting weight gains in the subject; (ii) lowering blood lipids; (iii) lowering fasting blood glucose levels; (iv) increasing glucose tolerance. According to a preferred embodiment of the present invention, C57bL/6 mice are used as test mice, and fed with a high-fat diet and injected with *Streptomyces* urea (STZ) for the induction to obtain a type 2 diabetes (T2D) model mouse, the T2D model mice treated with the *Faecalibacterium longum* CM04-06 strain have a slower weight gain and decreased blood lipids compared with the untreated control group (model group), and various diabetes-related indicators are also decreased, such as fasting blood glucose levels. In addition, sugar tolerance has also been improved significantly. Therefore, the strain can be used for the prevention and treatment of diabetes and related diseases (such as cardiovascular disease, obesity, etc.).

Composition and the Use Thereof

The invention also provides a composition, preferably a pharmaceutical composition. The composition includes an effective amount of *Faecalibacterium longum*, and in a preferred embodiment, the composition further comprises a milk growth factor. In a preferred embodiment, the composition further comprises a probiotic selected from the group consisting of: *Lactobacillus*, bifidobacteria, *Lactobacillus acidophilus*, and a combination thereof; and/or a prebiotic selected from the group consisting of: fructo-oligosaccharide (FOS), galactooligosaccharide (GOS), xylooligosaccharide (XOS), lactosucrose (LACT), soybean oligosaccharides (SOS), Inulin, and a combination thereof.

In a preferred embodiment, the composition is a liquid preparation, a solid preparation, or a semi-solid preparation.

In a preferred embodiment, the liquid preparation is selected from the group consisting of a solution product and a suspension product.

In a preferred embodiment, the dosage form of the composition is selected from the group consisting of powder, pulvis, tablet, sugar coating agent, capsule, granule, suspending agent, solution, syrup, drop, and sublingual tablet.

The pharmaceutical composition of the present invention may be administered in any form selected from the group consisting of a pharmaceutical tablet, injection and capsule. The pharmaceutical preparation comprises an excipient, and a pharmaceutically acceptable vehicle or a carrier, and these substances may be selected according to the administration route. The pharmaceutical preparations in the present invention may further contain auxiliary active ingredients.

Lactose, glucose, sucrose, sorbitol, mannose, starch, arabic gum, calcium phosphate, alginate, gelatin, calcium silicate, fine crystalline cellulose, polyvinylpyrrolidone (PVP), cellulose, water, syrup, methyl cellulose, methyl hydroxybenzoate, propyl hydroxybenzoate, talc, magnesium stearate, or mineral oil and the like can all be used as a carrier, an excipient or a diluent and the like in the pharmaceutical composition of the present invention.

In addition, the pharmaceutical composition of the present invention may further include a lubricant, wetting agent, emulsifying agent, suspension stabilizer, preservative, sweetener and fragrance and the like. The pharmaceutical composition of the present invention can be produced as enteric-coated preparations by various well-known methods so that the active ingredient of the pharmaceutical composition, that is, the microorganisms, can pass through the stomach without being destroyed by gastric acid.

In addition, the microorganism of the present invention can be used in the form of a capsule prepared by a conventional method. For example, a standard excipient is mixed with the freezing-dried microorganisms of the present invention to form a pellet pill, and then the pill is filled into a gelatin capsule. Further, the microorganisms of the present invention can be mixed with a pharmaceutically acceptable excipient, such as a liquid gum, cellulose, silicate or mineral oil and the like to prepare a suspension or a dispersion liquid, which can be filled into a soft gelatin capsule.

The pharmaceutical composition of the present invention can be made into enteric-coated tablets for oral use. The term "enteric coating" in the present invention includes all the conventional and pharmaceutically acceptable coatings. These coatings cannot be degraded by gastric acid but can be sufficiently decomposed in the small intestine and the microorganisms of the present invention can be released rapidly. The enteric coating of the present invention can be maintained in a synthetic gastric acid, such HCl solution (pH=1), for more than 2 hours at 36-38° C. and preferably can be decomposed within 1.0 hour in a synthetic intestinal fluid, such as buffer with a pH of 7.0.

The enteric coating of the present invention is coated at about 16-30 mg, preferably 16-25 mg, more preferably 16-20 mg, per tablet. The thickness of the enteric coating in the present invention is 5-100 μm, and the ideal thickness is 20-80 μm. The ingredient of the enteric coating is selected from conventional polymers that are well known in the art.

The preferred enteric coating of the present invention can be prepared from a copolymer of a cellulose acetate phthalate polymer or a trimellitate polymer and a methacrylic acid (for example, a methacrylic acid copolymer containing 40% or more of methacrylic acid and methylcellulose hydroxypropyl phthalate or the ester derivatives thereof).

The cellulose acetate phthalate used in the enteric coating of the present invention has a viscosity of about 45-90 cp. The content of the acetyl is 17-26%, and the content of orthophthalic acid is 30-40%. The cellulose acetate diphenyl ester used in the enteric coating has a viscosity of about 5-21 cs. The content of acetaphthalein is 17-26%. The cellulose acetate trimellitate manufactured by Eastman Keda Company can be used for the enteric coating materials in the present invention.

The hydroxypropylmethylcellulose phthalate used in the enteric coating of the present invention typically has a molecular weight of 20,000-130,000 Daltons, and the ideal molecular weight is 80,000-100,000 Daltons. The content of the hydroxypropyl is 5-10%, the methoxy content is 18-24% and the phthaloyl content is 21-35%.

The hydroxypropylmethylcellulose phthalate used in the enteric coating of the present invention is HP50, produced by Shin-Etsu Chemical Co., Ltd., Japan. HP50 with a molecular weight of 84,000 Daltons contains 6-10% of hydroxypropyl, 20-24% of methoxy, and 21-27% of propyl. Another enteric coating material is HP55, and HP55 with a molecular weight of 78,000 Daltons contains 5-9% of hydroxypropyl methylcellulose phthalate, 18-22% of methoxy, and 27-35% of phthalic acid.

The enteric coating of the invention is prepared by spraying the enteric coating solution onto the core using conventional methods. All of the solvents in the enteric coating process are alcohols (such as, ethanol), ketones (such as, acetone), halogenated hydrocarbon compounds (such as, methylene chloride), or a combination thereof. The softener, such as di-n-butyl phthalate or triacetin, is added into the enteric-coated solution at a ratio of about 1 part of the coating to about 0.05 parts or about 0.3 parts of a softener. The spraying method is preferably continuously carried out and the amounts of spraying materials can be controlled according to the conditions used for the coating. Spraying pressure can be adjusted randomly. In general, the desired results can be obtained at an average pressure of 1-1.5 bar.

The term "pharmaceutically effective amount" in the specification refers to an amount that is functional and active to human and/or animals and acceptable to human and/or animals. For example, in the present invention, a preparation containing $1\times10$-$1\times10^{10}$ cfu/ml or cfu/g (particularly, $1\times10^4$-$1\times10^{10}$ cfu/ml or cfu/g; more particularly, $1\times10^6$-$1\times10^{10}$ cfu/nil or cfu/g) of *Faecalibacterium longum* and/or a metabolite thereof.

When used for the preparation of pharmaceutical compositions, the effective dosage of *Faecalibacterium longum* or the metabolites thereof may vary depending on the mode of administration and the severity of the disease to be treated. Dosage forms suitable for oral administration include about $1\times10$-$1\times10^{10}$ cfu/ml or cfu/g (particularly, $1\times10^4$ to $1\times10^{10}$ cfu/ml or cfu/g; more particularly $1\times10^6$ to $1\times10^{10}$ cfu/ml or cfu/g) of the active *Faecalibacterium longum* or active fermentation products, in a close mixture with a solid or a liquid pharmaceutically acceptable carrier. This dosing regimen can be adjusted to provide the best therapeutic response. For example, depending on the urgency of the treatment condition, several divided doses may be administered daily, or the dose may be proportionally reduced.

The *Faecalibacterium longum* or the metabolites thereof can be administered by oral administration and the like. Solid carriers include starch, lactose, dicalcium phosphate, microcrystalline cellulose, sucrose and kaolin, and liquid carriers include: medium, polyethylene glycol, nonionic surfactants and edible oils (such as corn oil, peanut oil, and sesame oil), as long as it is suitable for the properties of the *Faecalibacterium longum* or the metabolites thereof and the desired particular mode of administration. Adjuvant commonly used in the preparation of pharmaceutical compositions, for example, flavors, coloring agents, preservatives and antioxidants such as vitamin E, vitamin C, BHT and BHA, may also be advantageously included.

In order to facilitate preparation and administration, the preferable pharmaceutical compositions are solid compositions, especially tablets and solid-filled or liquid-filled capsules. Oral administration is preferred.

The composition of the invention is administered to the individual one or more times per day. The dosage unit means that the dose is formally separable and suitable for human or other mammalian individual. Each unit contains a pharmaceutically acceptable carrier and a therapeutically effective amount of the microorganism of the present invention. The amount to be administered varies with the weight of the patient, the severity of the obesity, the included supplementary active components and the employed microorganisms. In addition, if possible, they can be administered separately and, if necessary, they can be administered continuously. Thus, the amounts for administration will not limit the invention. In addition, the "composition" in the present invention not only means medicines but also functional food and health supplements. In a preferred embodiment, the composition comprises: beverage, food, medicine, animal feed and the like.

In a preferred embodiment of the present invention, a food composition is further provided, comprising an effective amount of *Faecalibacterium longum* and/or a metabolite thereof, and the rest food acceptable carrier, the dosage form of the food composition is selected from the group consisting of a solid, dairy product, solution product, powder product, and suspension product. In a preferred embodiment, the food composition can further contain milk growth factor.

In a preferred embodiment, the formulation of the composition is shown as follows:

$1\times10$-$1\times10^{10}$ cfu/mL of *Faecalibacterium longum* and/or the metabolites thereof; and a food or pharmaceutically acceptable carrier, and/or an excipient.

In another preferred embodiment, the formulation of the composition is shown as follows: $1\times10^{6}$-$1\times10^{10}$ cfu/mL of *Faecalibacterium longum* and/or the metabolites thereof; and a food or pharmaceutically acceptable carrier, and/or an excipient.

Microecological Preparation

The microecological preparation is a biological preparation containing a probiotic and metabolite or a dietary supplement which can increase probiotics, and can achieve the purpose of improving human health by regulating and maintaining the microecological balance in the intestinal tract. It mainly includes probiotics, prebiotics and synbiotics.

In the present invention, the microecological preparation comprises (a) a safe and effective amount of the *Faecalibacterium longum* and/or the metabolite thereof; and (b) a food acceptable carrier or a pharmaceutically acceptable carrier. In a preferred embodiment, the formulation further comprises a growth factor (such as milk growth factor, preferably including vitamins, purines and/or pyrimidines).

Production Method for *Faecalibacterium longum*

Generally, *Faecalibacterium longum* can be prepared by conventional methods.

In the present invention, a method capable of producing *Faecalibacterium longum* on a large scale is provided. In particular, the following steps are included:

(a) under conditions suitable for cultivation, cultivating *Faecalibacterium longum*, thereby obtaining a culture product;

(b) optionally, isolating the *Faecalibacterium longum* thalluses and/or metabolites thereof from the culture product; and (c) optionally, mixing the isolated *Faecalibacterium longum* thalluses and/or their metabolites obtained in the previous step with a food acceptable carrier or pharmaceutically acceptable carrier, thereby preparing a composition.

Method for Reducing the Weight, Fasting Blood Glucose and/or Blood Lipid

In another preferred embodiment, the method comprises: ingesting a pharmaceutical composition, a food composition, a beverage composition, or the combination thereof of the present invention. The subject is human.

In another preferred embodiment, the method comprises: ingesting a pharmaceutical composition, a food composition, or an animal feed of the invention, or a combination thereof.

The subjects are animals, preferably mice and rabbits.

Method for Improving Sugar Tolerance

In another preferred embodiment, the method comprises: ingesting a pharmaceutical composition, a food composition, a beverage composition, or the combination thereof of the present invention. The subject is human.

In another preferred embodiment, the method comprises: ingesting a pharmaceutical composition, a food composition, or an animal feed of the invention, or a combination thereof. The subjects are animals, preferably mice and rabbits.

Deposit of Microorganisms

The strain of *Faecalibacterium longum* (*Faecalibacterium longum* CM04-06) (with the same deposit name) of the present invention has been deposited at the China General Microbiological Culture Collection Center (CGMCC, address: No. 3, NO. 1 of West Beichen Road, Chaoyang District, Beijing, China) on Jun. 13, 2016, deposit number: CGMCC 1.5208.

The main advantages of the invention include:

(a) The *Faecalibacterium longum* of the present invention can significantly reduce body weight, lower blood lipids and fasting blood glucose levels.

(b) The *Faecalibacterium longum* of the present invention can significantly reduce indicators associated with obesity and related diseases such as cardiovascular diseases (such as cholesterol and triglycerides).

(c) The *Faecalibacterium longum* of the present invention can significantly reduce the levels of total cholesterol, triglyceride, and low density lipoprotein.

(d) The *Faecalibacterium longum* of the present invention can significantly increase the level of high density lipoprotein.

(e) The *Faecalibacterium longum* of the present invention can significantly improve the sugar tolerance.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions. Unless otherwise stated, the materials used in the examples are all commercially available products. *Faecalibacterium prausnitzii* ATCC 27768, hereinafter referred to as ATCC 27768, was purchased from the American Type Culture Collection with the deposit number of ATCC 27768.

Example 1 Screening and Identification of *Faecalibacterium longum* CM04-06

1.1 Isolation and Cultivation of CM04-06

The *Faecalibacterium longum* CM04-06 (hereinafter referred to as CM04-06) of the present invention was isolated from faeces sample of a healthy child (male) in Shenzhen. The environment for isolation and cultivation was strictly anaerobic conditions. The specific isolation process was: about 0.2 g of faeces sample was taken in the anaerobic operation box, 1 ml of sterile PBS was used for suspension and dispersion, a gradient dilution coating was performed after fully shaking and mixing. The medium was anaerobic PYG medium (purchased from Huan Kai Microbiology Technology Co., Ltd.), and the specific components were shown in the table below:

TABLE 1

| component | content (1 L) |
| --- | --- |
| peptone | 5 g |
| trypticase peptone | 5 g |
| yeast powder | 10 g |
| beef extract | 5 g |
| glucose | 5 g |
| $K_2HPO_4$ | 2 g |
| sodium acetate | 5 g |
| Cysteine-HCl·$H_2O$ | 0.5 g |
| protoheme | 5 mg |
| inorganic salt solution | 40 ml |
| resazurin | 1 mg |
| distilled water | 950 ml |

The formulation of the inorganic salt solution was:

| inorganic salt component | content (1 L) |
| --- | --- |
| $CaCl_2·2H_2O$ | 0.25 g |
| $MgSO_4·7H_2O$ | 0.5 g |
| $K_2HPO_4$ | 1 g |

-continued

| inorganic salt component | content (1 L) |
| --- | --- |
| $KH_2PO_4$ | 1 g |
| $NaHCO_3$ | 10 g |
| NaCl | 2 g |

The coated plate was cultured under anaerobic conditions at 37° C. for 3-4 days. After the colony was grown on the surface of the plate, a single colony was picked for the separation until the pure culture strain was obtained, and the isolated strain was cryopreserved at −80° C. using glycerol.

1.2 Identification for 16S rDNA of *Faecalibacterium longum* CM04-06

(1) Extraction of the genome: The isolated strain was cultured, and when the concentration of the bacteria reached the order of $10^8$ cfu/ml, 2 ml of the bacterial liquid was taken for the genomic DNA extraction.

(2) PCR amplification of 16S rDNA: 16S rDNA amplification was performed using DNA as a template, and 16S rDNA universal amplification primers were selected as amplification primers: 8F-1492R (5'-AGAGTTTGAT-CATGGCTCAG-3' (SEQ ID NO.: 2) and 5'-TAGGGTTAC-CTTGTTACGACTT-3' (SEQ ID NO.: 3)), the PCR amplification program was shown as follows:

| | | |
| --- | --- | --- |
| 94° C. | 4 min | |
| 94° C. | 30 s | |
| 65° C.-57° C. | 40 s | 20 cycles |
| 72° C. | 1 min 30 s | |
| 94° C. | 30 s | |
| 57° C. | 40 s | |
| 72° C. | 1 min 30 s | 10 cycles |
| 72° C. | 10 min | |
| 4° C. | ∞ | |

(3) Purification and sequencing: The PCR product was obtained for magnetic bead purification, and then subjected to electrophoresis detection. The band position of 16S rDNA was about 1.5 k, and the purified product was subjected to 3730 sequencing.

(4) 16S rDNA sequence database alignment: a 1372 bp 16S rDNA sequence was obtained by sequencing, and the sequence was aligned in the EzTaxon-e database to preliminarily obtain the species classification information of the strain. According to the information of 16S rDNA, it can be preliminarily determined that CM04-06 was a new species belonging to the genus *Faecalibacterium*.

The 16S rDNA sequence of CM04-06 was SEQ ID NO.: 1, shown as below:

```
caagtcgaac gagagatgag gagcttgctc ttcagatcga gtggcgaacg ggtgagtaac    60
gcgtgaggaa cctgcctcaa agaggggggac aacagttgga aacgactgct aataccgcat   120
aagcccacgg ctcggcatcg agcagaggga aaaggagtga tccgctttga gatggcctcg   180
cgtccgatta gctggttggt gaggtaacgg cccaccaagg cgacgatcgg tagccggact   240
gagaggttga acggccacat tgggactgag acacggccca gactcctacg ggaggcagca   300
gtggggaata ttgcacaatg ggggaaaccc tgatgcagcg acgccgcgtg gaggaagaag   360
gtcttcggat tgtaaactcc tgttgttgag gaagataatg acggtactca acaaggaagt   420
gacggctaac tacgtgccag cagccgcggt aaaacgtagg tcacaagcgt tgtccggaat   480
tactgggtgt aaagggagcg caggcgggag aacaagttgg aagtgaaatc catgggctca   540
```

```
                                    -continued
acccatgaac tgctttcaaa actgttttc ttgagtagtg cagaggtagg cggaattccc    600
ggtgtagcgg tggaatgcgt agatatcggg aggaacacca gtggcgaagg cggcctactg    660
ggcaccaact gacgctgagg ctcgaaagtg tgggtagcaa acaggattag ataccctggt    720
agtccacacc gtaaacgatg attactaggt gttggaggat tgaccccttc agtgccgcag    780
ttaacacaat aagtaatcca cctggggagt acgaccgcaa ggttgaaact caaaggaatt    840
gacgggggcc cgcacaagca gtggagtatg tggtttaatt cgacgcaacg cgaagaacct    900
taccaagtct tgacatccct tgacgaacat agaaatattt tttctcttcg gagcaaggag    960
acaggtggtg catggttgtc gtcagctcgt gtcgtgagat gttgggttaa gtcccgcaac   1020
gagcgcaacc cttatggtca gttactacgc aagaggactc tggccagact gccgttgaca   1080
aaacggagga aggtggggat gacgtcaaat catcatgccc tttatgactt gggctacaca   1140
cgtactacaa tggcgttaaa caaagagaag caagaccgcg aggtggagca aaactcagaa   1200
acaacgtccc agttcggact gcaggctgca actcgcctgc acgaagtcgg aattgctagt   1260
aatcgtggat cagcatgcca cggtgaatac gttcccgggc cttgtacaca ccgcccgtca   1320
caccatgaga gccgggggga cccgaagtcg gtagtctaac cgcaaggagg ac           1372
```

1.3 16S rDNA evolution analysis of CM04-06

The 16S rDNA sequence was used for the evolution analysis of CM04-06, the alignment was performed using EzTaxon-e database by the 16S rDNA sequence of CM04-06, and the species closely related to CM04-06 was obtained. Sequence alignment was performed for the 16S rDNA sequence of these species and CM04-06 and then the neighbor-joining evolutionary tree was drawn using the Mega5 software.

1.4 Microbiological Characteristics of CM04-06

(1) Morphological characteristics: CM04-06 was cultured at 37° C. in an anaerobic environment for 2-3 days. The colonies were yellowish white, with high water content, a little sticky, nearly round, opaque, flat with a bulge in the middle, and the colony diameter was about 2-3 mm (FIG. 1).

Figure 2:
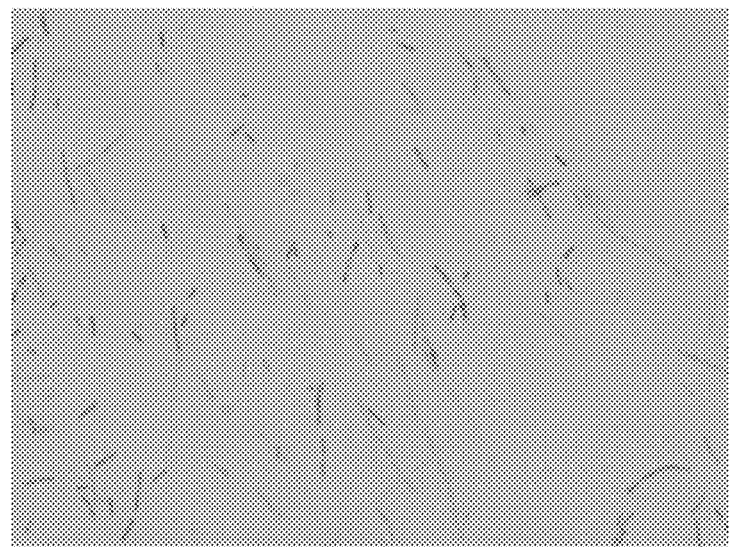
FIG. 2 shows a microscopic image (1000 fold) of *Faecalibacterium longum* of the present invention stained by Gram's method.

(2) Microscopic characteristics: under the microscope magnification of 1000 times, the bacteria cells of CM04-06 were long rod-shaped, and the Gram staining reaction was negative, no spores and flagella were found. The diameter of the bacteria cells was about 1 um and the length was 4-10 um (FIG. 2).

(3) Physiological and biochemical characteristics: both oxidase and catalase reactions were negative, the growth temperature ranged from 30 to 45° C., the pH ranged from 4.0 to 9.0, and the optimum temperature and pH were 37° C. and pH 7.0. It can tolerate 3% NaCl. The comparison of the physiological and biochemical reactions of CM04-06 with the closest reference strain ATCC 27768 (including substrate utilization situation API 20A and enzyme reaction API ZYM) was shown as follows: (+, indicating positive reaction; −, indicating negative reaction; w, indicating weak positive reaction).

TABLE 2

| Substrate | CM04-06 | Faecalibacterium prausnitzii ATCC 27768 |
|---|---|---|
| API 20A | | |
| Tryptophan (produced by indole) | − | − |
| Urea (urease) | − | − |
| glucose | − | − |

TABLE 2-continued

| Substrate | CM04-06 | Faecalibacterium prausnitzii ATCC 27768 |
|---|---|---|
| mannitol | − | − |
| lactose | − | − |
| sucrose | − | − |
| maltose | − | − |
| salicin | − | − |
| xylose | − | − |
| arabinose | − | − |
| gelatin hydrolysate | + | − |
| esculin/ferric citrate | − | + |
| glycerin | − | − |
| Cellobiose | − | − |
| Mannose | + | − |
| melezitose | − | − |
| raffinose | w | − |
| sorbitol | − | − |
| rhamnose | − | − |
| trehalose | w | − |
| API ZYM | | |
| control | − | − |
| Alkaline phosphatase | − | − |
| Esterase (C4) | − | w |
| Lipid esterase (C8) | − | − |
| Lipid enzyme (C14) | − | − |
| Leucine arylamidase | − | − |
| Proline arylamidase | w | − |
| Cystine arylamidase | w | − |
| Trypsin | − | − |
| chymotrypsin | + | − |
| acid phosphatase | − | − |
| naphthol-AS-BI-phosphohydrolase | − | + |
| α-galactosidase | − | − |
| β-galactosidase | − | − |
| β-glucuronidase | w | − |
| α-glucosidase | − | + |
| β-glucosidase | − | − |
| N-acetyl-glucosaminidase | w | − |
| α-mannosidase | − | − |
| β-fucosidase | − | − |

Comparison of physiological and biochemical reactions of the above CM04-06 with reference bacteria showed that the utilizaiton of raffinose and trehalose, hydrolysis of esculin and gelatin, and the activity of esterase (C4), proline arylamidase, cystine arylamidase, chymotryp sin, naphthol-AS-BI-phosphohydrolase, β-glucuronidase, α-glucosidase and N-acetyl-glucosaminidase for CM04-06 were significantly different, it can be shown that CM04-06 is a new species different from the known bacteria.

1.5 Analysis on Cellular Fatty Acids

The bacteria cells cultured to the stable phase of CM04-06 and *Faecalibacterium prausnitzii* ATCC 27768 (hereinafter referred to as ATCC 27768, purchased from the American Type Culture Collection (the deposit number was ATCC 27768)) were collected and then subjected to the extraction and detection of cellular fatty acids. The content and difference of fatty acid components of the two strains of bacteria cells were analyzed by gas chromatography.

TABLE 3

| Fatty acids | Chinese name | ATCC 27768 | CM04-06 |
|---|---|---|---|
| $C_{12:0}$ | saturated C12 fatty acid | 1.92 | 1.75 |
| $C_{13:1}$ | monounsaturated C13 fatty acid | 1.25 | 0 |
| $C_{14:0}$ | saturated C14 fatty acid | 11.80 | 4.61 |
| $C_{13:0}$ 3OH/$C_{15:1}$ iso I | 3-hydroxy saturated C13/ type I-iso monounsaturated C15 fatty acid | 2.14 | 0 |
| $C_{15:0}$ anteiso | trans-iso saturated C15 fatty acid | 0 | 2.60 |
| $C_{16:1}$ ω7c/$C_{16:1}$ ω6c | ω7c/ω6c-monounsaturated C16 fatty acid | 4.02 | 1.92 |
| $C_{16:0}$ | saturated C16 fatty acid | 21.07 | 25.53 |
| $C_{17:1}$ iso I/anteiso B | Type I-iso/type B-trans-iso unsaturated C17 fatty acid | 7.63 | 9.74 |
| $C_{17:0}$ anteiso | trans-iso saturated C17 fatty acid | 0 | 2.09 |
| $C_{17:1}$ ω8c | ω8c-monounsaturated C17 fatty acid | 1.12 | 0 |
| $C_{18:0}$ antei/$C_{18:2}$ ω6, 9c | trans-iso saturated C18 fatty acid/ω 6,9c-diunsaturated C18 fatty acid | 1.31 | 1.93 |
| $C_{18:1}$ ω9c | ω9c-diunsaturated C18 fatty acid | 31.42 | 32.51 |
| $C_{18:1}$ ω7c | ω7c-diunsaturated C18 fatty acid | 5.74 | 7.46 |
| $C_{18:0}$ | saturated C18 fatty acid | 4.11 | 3.53 |
| $C_{19:1}$ iso I | Type I-iso monounsaturated C19 fatty acid | 2.12 | 1.12 |

TABLE 3-continued

| Fatty acids | Chinese name | ATCC 27768 | CM04-06 |
|---|---|---|---|
| $C_{19:0}$ iso | iso-saturated C19 fatty acid | 0 | 5.91 |
| $C_{18:1}$ 2OH | 2-hydroxy diunsaturated C18 fatty acid | 1.95 | 0 |

Based on the above CM04-06 phenotype, 16S rDNA sequence and physiological and biochemical reactions, it showed that CM04-06 was a new species, which was named as *Faecalibacterium longum*.

Example 2 Biologically Active Substance of *Faeccalibacterium longum* CM04-06

2.1 Detection of Short Chain Fatty Acids (SCFA)

(1) Sample preparation: 1 ml of CM04-06 bacterial solution cultured for 48 hours, centrifuged at 12000 r/min for 5 min, and the supernatant was removed, ready for use.

(2) Determination of SCFA: Short-chain fatty acid was determined by external standard method, and acetic acid, propionic acid, butyric acid, and pentanoic acid were used to prepare a standard curve. Agilent Gas Chromatograph (GC-7890B, Agilent), HP-INNOWax (Cross-Linked PEG), 30 m×0.25 mm×0.25 um capillary column was used for analysis. The detector was a hydrogen flame ion detector, and the GC parameters were set to: Column temperature: 180~200° C.; gasification chamber temperature: 240° C.; detect temperature: 210° C.; sample size: 2 μL; carrier gas flow rate: $N_2$, 50 mL/min; hydrogen flow rate: 50 mL/min; air flow rate: 600~700 mL/min.

(3) Results: The SCFA yield was determined as: formic acid (7.62 mmol/L), acetic acid (44.8 mmol/L), butyric acid (40.03 mmol/L).

2.2 Detection of Organic Acids (1) Sample preparation: same as section 2.1.

(2) Determination of organic acids: 3-methylbutyric acid, pentanoic acid, quininic acid, lactic acid, oxalic acid, malonic acid, benzoic acid, maleic acid, succinic acid, transfumaric acid, malic acid, hexanedioic acid, tartaric acid, shikimic acid, citric acid, isocitric acid and L-ascorbic acid were selected for the organic acid detection standards. Agilent Gas Chromatograph (GC-7890B, Agilent) was still used, the column was 122-5532G DB-5 ms (40 m×0.25 mm×0.25 um), column temperature: 270~290° C.; inlet temperature: 250° C.; gas flow rate: 0.86 mL/min.

(3) Results: The determined organic acid yields were shown in the following table (Table 4).

TABLE 4

| Organic acid | 3-methylbutyric acid | pentanoic acid | quininic acid | lactic acid | oxalic acid | malonic acid |
|---|---|---|---|---|---|---|
| content (mmol/L) | 0.26 | 0.49 | 0 | 30.53 | 0 | 0 |
| Organic acid | benzoic acid | maleic acid | succinic acid | transfumaric acid | malic acid | hexanedioic acid |
| content (mmol/L) | 1.79 | 0 | 0.88 | 0 | 0 | 0.60 |
| Organic acid | tartaric acid | shikimic acid | citric acid | isocitric acid | L-ascorbic acid | |
| content (mmol/L) | 0 | 0 | 0. | 0 | 0.11 | |

Example 3 Detection of Extracellular Polysaccharide Produced by *Faecialbacterium longum* CM04-06

The detection of extracellular polysaccharides was carried out by the sulfuric acid phenol method. The sulfuric acid phenol can react with free monosaccharides, oligosaccharides and hexoses in the polysaccharides, and the color produced is proportional to the absorbance, and the absorption wavelength is 490 nm. The specific experimental process was as follows:

(1) Extraction of Polysaccharides

The experimental strain was cultured in PYG medium (formulation was the same as that in Example 1) for 2 days, 10 ml of bacteria solution was taken and treated in boiling water bath for 30 min, then centrifuged at 10000 r/min, and the supernatant was taken, and 80% trichloroacetic acid was added to a final concentration of 8%. The protein was precipitated by treatment at 4° C. overnight. It was centrifuged at 10,000 r/min for 30 min, and the pH of the supernatant was adjusted to 6.0 with NaOH. 2 times volume of absolute ethanol was added to precipitate the polysaccharide, treated at 4° C. overnight, it was taken and centrifuged at 10000 r/min for 30 min, the supernatant was removed, the precipitate was dissolved with preheated distilled water, and transferred to the ultrafiltration tube (3000 Da of filter diameter) for the ultrafiltration, the centrifugation was performed at 5000 r/min for 30 min, the polysaccharide intercepted in the inner tube was transferred to a volumetric flask to a volume of 10 ml with a distilled water, and ready for use.

(2) Production of Glucose Standard Curve 20 mg of standard glucose was accurately weighed and added to 100 ml of volumetric flask, the water was added to the tick mark, and then 20, 40, 60, 80, and 100 μg/ml of the glucose standard solution were separately prepared. 400 ul standard solution was taken for each group, there are three parallel groups, and then 400 ul of 5% phenol and 1 ml of concentrated sulfuric acid were sequentially added to carry out the reaction, and the mixture was in a boiling water bath for 15 minutes and then cooled to room temperature, and the absorbance at 490 nm was measured. Then, the absorbance was used as the ordinate, and the glucose standard solution concentration was used as the abscissa for the standard curve.

(3) Detection of the Concentration of the Extracted Polysaccharide 400 ul of the polysaccharide solution was taken, and 400 ul of 5% phenol and 1 ml of concentrated sulfuric acid were successively added to carry out the reaction, and the mixture was in a boiling water bath for 15 minutes and then cooled to room temperature, and the absorbance at 490 nm was measured. The concentration of the polysaccharide was calculated from the glucose standard curve.

(4) Results

By calculation, the content of extracellular polysaccharide in CM04-06 fermentation liquid cultured for 2 days was 233 mg/L.

Example 4 In Vivo Test of *Faeccalibacterium Longum* CM04-06 in an Animal Model of Diabetes In this example, a type 2 diabetes (T2D) model mice was induced by high-fat diet feeding and injection of *Streptomyces* urea (STZ). The mice were treated with *Faeccalibacterium longum* CM04-06 for 2 months by gavage to investigate the therapeutic effect of CM04-06 on type 2 diabetes (T2D).

4.1 Modeling of T2D mice: C57bL/6 mice were used as the test mice (purchased from Hubei Medical Experimental Animal Center) with 8 weeks old. The experimental environment of the mice was SPF grade, adaptive feeding was performed for 1 week for group modeling. The modeling method was performed by the induction of high fat plus STZ, and when the fasting blood glucose level (FBG) reached more than 10 mM/L, it can be used as the T2D model mice.

4.2 Experimental Grouping:

(1) Model group: the T2D model mice were intragastrically administered with normal saline;

(2) CM04-06 treatment group: the T2D model mice were intragastrically treated with CM04-06 bacterial solution;

(3) Positive drug group: the T2D model mice were treated for intervention with the positive drug metformin.

4.3 Preparation of bacterial solution: CM04-06 was cultured to a stable phase, and the concentration of bacteria was about $10^8$ cfu/ml.

4.4 Test procedure: The experiment was carried out according to the grouping situation, and the treatment was started after T2D modeling (FBG>10), and the treatment lasted for 2 months. The feeding activity of the mice was recorded daily, and the body weight was weighed. The tail vein blood was collected weekly, the fasting blood glucose level of the mice was measured, and the glucose tolerance (OGTT) of the mice was measured at the fourth week of treatment and at the end of the experiment. The mice were sacrificed 2 months after the test. The eyeballs of all mice were harvested for blood collection and the necks were removed. The total cholesterol (TC), triglyceride (TG), high density lipoprotein cholesterol (HDL-C) and low density lipoprotein cholesterol (LDL-C) in serum were detected.

Figure 3:
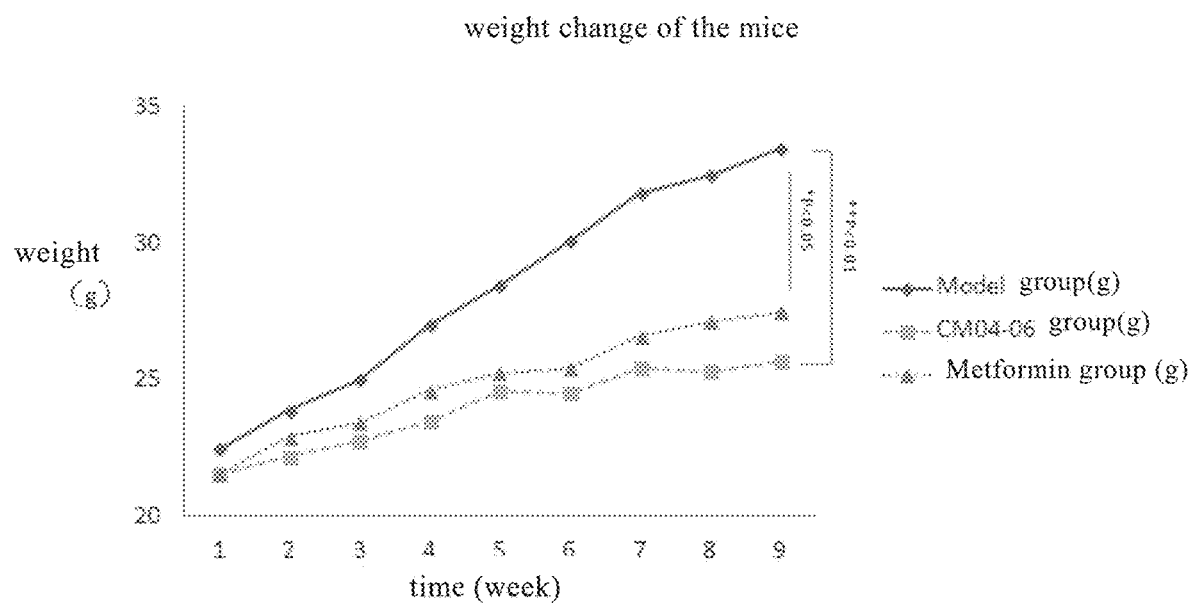
FIG. 3 shows the changes in body weight of the model group and the diabetic mice treated with *Faecalibacterium longum* CM04-06 and metformin.

4.5 Experimental Results and Analysis (1) Body weight change: As shown in Table 5 and FIG. 3, as the test went on, the body weight of the mouse was gradually increased, the mice in the CM04-06 and metformin treatment groups gained less weight gain than the model group. It indicated that CM04-06 can effectively slow the increase of body weight in mice (*P<0.05/**P<0.01). At the same time, through statistics, CM04-06 was more effective in controlling the weight gain of mice than metformin.

TABLE 5

| Group number | 1 week | 3 weeks | 5 weeks | 7 weeks | 9 weeks |
|---|---|---|---|---|---|
| Model group (g) | 22.48 | 24.99 | 28.42 | 31.81 | 33.45 |
| CM04-06 group (g) | 21.56 | 22.76 | 24.59 | 25.41 | 25.65** |
| Metformin group (g) | 21.54 | 23.42 | 25.23 | 26.6 | 27.49* |

(2) Experimental Results of CM04-06 on Fasting Blood Glucose in Mice

TABLE 6

| Group number | Week one | Week three | Week five | Week seven | Week nine |
|---|---|---|---|---|---|
| Model group (mmol/L) | 15.5 | 16.8 | 17.2 | 16.9 | 15.2 |
| CM04-06 group (mmol/L) | 16.2 | 15.2 | 13.4* | 10.8** | 8.2** |
| Metformin group (mmol/L) | 16.7 | 15.8 | 14.6 | 12.1* | 9.8** |

Figure 4:
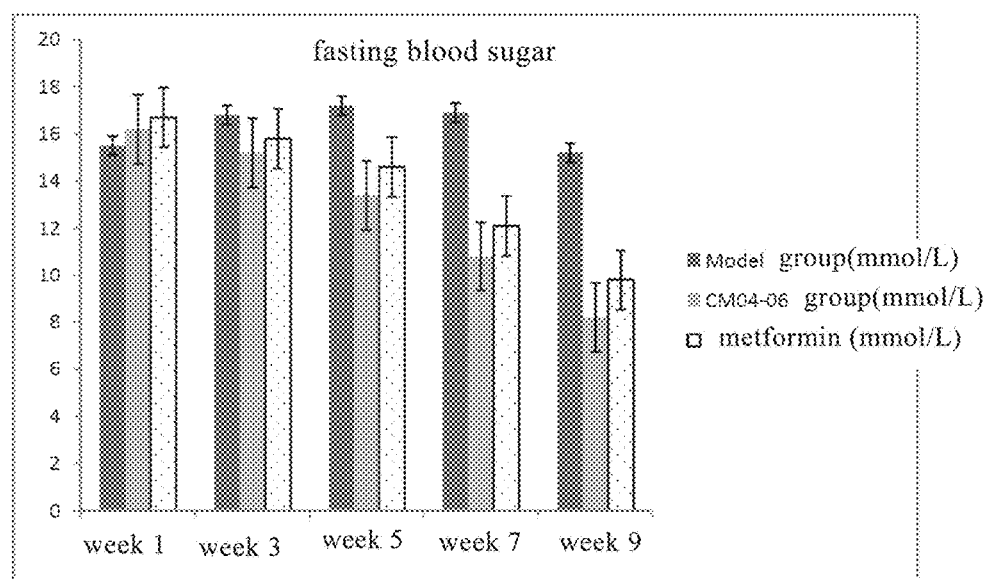
FIG. 4 shows the fasting blood glucose (FBG) results of the model group and the diabetic mice treated with *Faecalibacterium longum* CM04-06 and metformin.

According to the results in Table 6 and FIG. 4, the fasting blood glucose level of the mice in the CM04-06 and metformin groups was gradually decreased with the progress of the treatment, and the blood glucose level of the mice tended to be normal. The hypoglycemic effect is more significant, indicating that CM04-06 can effectively lower blood glucose (*P value<0.05/**P<0.01 compared with model group). At the same time, the blood glucose level of the mice in the CM04-06 group was lower than that in the metformin group. As it can be seen that the ability of CM04-06 to lower fasting blood glucose was better than that of metformin.

(3) Experimental Results of CM04-06 on Glucose Tolerance in Mice

Figure 5:
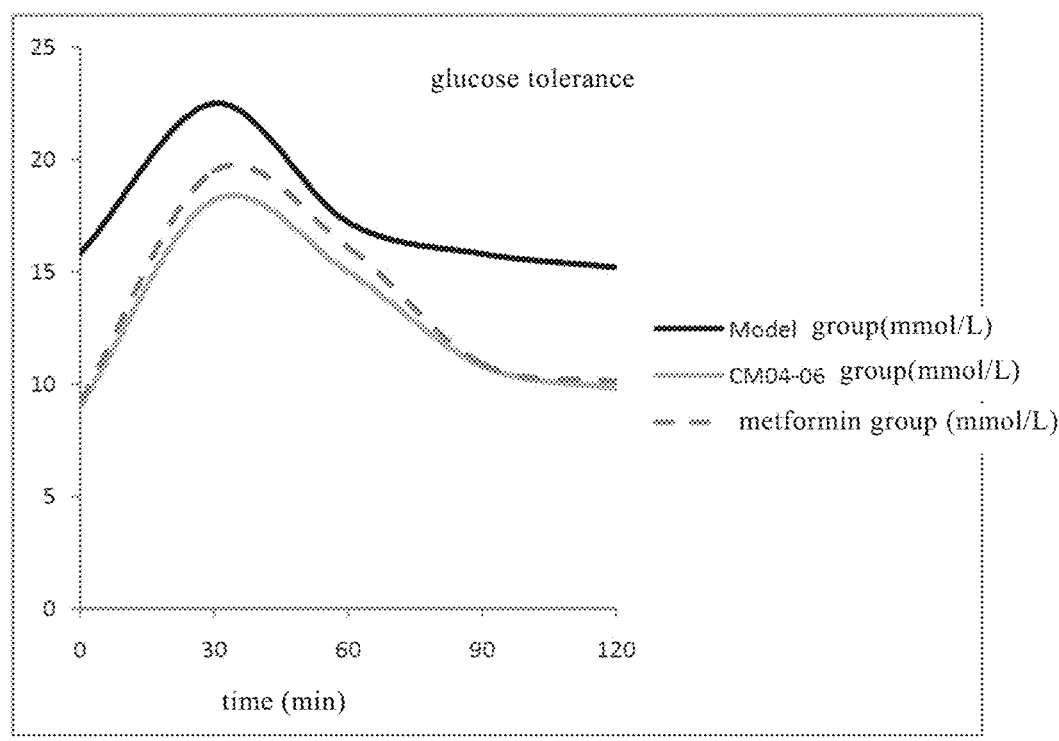
FIG. 5 shows the glucose tolerance results of the model group and the diabetic mice treated with *Faecalibacterium longum* CM04-06 and metformin.

By testing the glucose tolerance (OGTT) condition of the mice before sacrifice (Table 7 and FIG. 5), the results showed that after glucose administration by gavage, the blood glucose level of the mice reached the highest (18.2-22.5 mmol/L) after 30 minutes, and then the blood glucose level in metformin and CM04-06 groups was decreased at a constant rate, 9.8 mmol/L and 10.1 mmol/L at 120 min, while the blood glucose in the model group was 15.2. At this time point, the blood glucose level in the CM04-06 was significantly different from that in the model group (*P value<0.05). In terms of the overall process of glucose tolerance, by comparison, CM04-06 can effectively improve glucose intolerance in diabetic mice. During the whole process of glucose regulation, CM04-06 group had lower blood glucose levels than metformin group at various time points, which showed that CM04-06 had a better effect on improving glucose tolerance in diabetic mice.

TABLE 7

| Group number | 0 min | 30 min | 60 min | 90 min | 120 min |
|---|---|---|---|---|---|
| Model group (mmol/L) | 15.8 | 22.5 | 17.2 | 15.8 | 15.2 |
| CM04-06 group (mmol/L) | 9 | 18.2 | 15 | 10.8* | 9.8* |
| Metformin group (mmol/L) | 9.2 | 19.5 | 16.1 | 10.9* | 10.1* |

(4) Effect of CM04-06 on Blood Lipids in Mice

The blood lipids of the mice were determined after the end of the experiment, including total cholesterol (TC), triglyceride (TG), low density lipoprotein (LDLC) and high density lipoprotein (HDLC). The test results were shown in Table 8. The results showed that the low-density lipoprotein levels in the metformin group and the CM04-06 group were lower than that in the model group (*P value<0.05), and at the same time, the high-density lipoprotein levels were higher than that in the model group (*P value<0.05). The main function of high-density lipoprotein was to remove excess cholesterol and low-density lipoprotein in blood and cells, and it had anti-atherosclerosis effect. It can be seen that CM04-06 can improve hyperlipidemia symptoms in diabetic mice. At the same time, compared with the metformin group, CM04-06 had a better effect on the improvement of blood lipids, including lower LDL content and higher HDL content.

TABLE 8

| Group | TC (total cholesterol) (mmol/L) | TG (triglyceride) (mmol/L) | LDLC (low density lipoprotein) (mmol/L) | HDLC (high-density lipoprotein) (mmol/L) |
|---|---|---|---|---|
| Model group | 6.301 | 1.699 | 2.545 | 2.134 |
| Metformin group | 5.923 | 1.565 | 1.533* | 3.023* |
| CM04-06 group | 5.863 | 1.520 | 1.312* | 3.298* |

Example 5 Food Composition Containing *Faeccalibacterium longum* CM04-06

The formula ratio of raw materials was shown in Table 9.

TABLE 9

| raw materials | Mass percent (%) |
|---|---|
| *Faecalibacterium longum* CM04-06 | 0.5 |
| Milk | 90.0 |
| Sugar | 9.0 |
| Vitamin C | 0.5 |

The milk and sugar were mixed according to the above formula ratio, the mixture was stirred until completely mixed, preheated, homogenized at 20 Mpa, sterilized for 5-10 minutes at 90° C., cooled to 40-43° C., mixed with vitamin C, 1-100×10$^6$ cfu/g of the *Faecalibacterium longum* CM04-06 bacterium was inoculated, and then a food composition containing *Faecalibacterium longum* CM04-06 was obtained.

Example 6 Pharmaceutical Composition Containing *Faeccalibacterium longum* CM04-06

The formula ratio of raw materials was shown in Table 10.

TABLE 10

| Raw materials | Mass percent (%) |
|---|---|
| *Faecalibacterium longum* CM04-06 | 1.0% |
| lactose | 2.0% |
| yeast powder | 2.0% |
| peptone | 1.0% |
| purified water | 93.5% |
| Vitamin C | 0.5% |

According to the formula ratio, lactose, yeast powder and peptone were mixed uniformly with purified water, the mixture was preheated to 60-65° C., homogenized at 20 Mpa, sterilized at 90° C. for 20-30 minutes, cooled to 36-38° C., mixed with vitamin C, and *Faecalibacterium longum* CM04-06 live bacteria (1-50×10$^6$ cfu/mL) was inoculated, fermented to pH 6.0 at 36-38° C., centrifuged, freeze-dried to a moisture content of less than 3%, i.e., *Faecalibacterium longum* CM04-06 bacteria lyophilizate was prepared. 0.5 g of *Faecalibacterium longum* CM04-06 lyophilizate was weighed and mixed in an equal amount with maltodextrin and then filled into capsules to prepare a pharmaceutical composition containing *Faecalibacterium longum* CM04-06.

Example 7 Preparation of a Medicament Containing *Faeccalibacterium longum* CM04-06

7.1 Preparation of bacterial solution: *Faecalibacterium longum* CM04-06 (1×10$^9$ cfu/ml) was subjected to anaerobic culture, and PYG medium was used as an anaerobic medium, it was subjected to anaerobic fermentation at 37° C. for 2-3 days.

7.2 Preparation of growth factors: skim milk and casein were mixed and centrifuged, and subjected to ultrafiltration to obtain a crude extract of milk growth factor (containing nutrient substances such as vitamins, purines, and/or pyrimidines).

7.3 Preparation of pharmaceutical dosage form: 5 volumes of the above growth factor was added to 100 volumes of CM04-06 fermented bacterial solution and mixed well and then starch adjuvant (such as maltodextrin) was added to prepare and obtain a medicament containing *Faecalibacterium longum* CM04-06.

Deposit of Microorganisms

The strain of *Faecalibacterium longum* (*Faecalibacterium longum* CM04-06) (with the same deposit name) of the present invention has been deposited at the China General Microbiological Culture Collection Center (CGMCC, address: No. 3, NO. 1 of West Beichen Road, Chaoyang District, Beijing, China) on Jun. 13, 2016, deposit number: CGMCC 1.5208.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A method of treating diabetes or diabetes related diseases, which comprises a step of: administering a *Faecalibacterium longum* or a composition comprising the *Faecalibacterium longum* to a subject in need, wherein the *Faecalibacterium longum* has a sequence of 16s rDNA as set forth in SEQ ID NO: 1.

2. The method of claim 1, wherein the *Faecalibacterium longum* is *Faecalibacterium longum* CM04-06 with a deposit number of CGMCC 1.5208.

3. The method of claim 1, wherein the *Faecalibacterium longum* or the *Faecalibacterim longum* composition exhibits any activities from the group consisting of:
  (i) reduction of the weight gain in mammals;
  (ii) reduction of blood lipid level in mammals;
  (iii) increase of high density lipoprotein (HDL-C) level in mammals;
  (iv) reduction of low-density lipoprotein (LDL-C) level in mammals;
  (v) reduction of blood glucose level in mammals; and
  (vi) increase of glucose tolerance in mammals.

4. The method of claim 3, wherein the reduction of blood lipid level in mammals comprises the reduction of total cholesterol (TC) level or triglyceride level.

5. The method of claim 1, wherein the diabetes related diseases are cardiovascular diseases or obesity.

6. The method of claim 1, wherein the subject includes human or non-human mammal.

7. The method of claim 1, wherein the composition further comprises a food acceptable or pharmaceutically acceptable carrier.

8. The method of claim 1, wherein the composition further comprises probiotics and/or prebiotics.

9. The method of claim 8, wherein the probiotics are selected from the group consisting of *lactobacillus*, bifidobacteria, *Lactobacillus acidophilus*, and a combination thereof, and the prebiotics are selected from the group consisting of fructooligosaccharide (FOS), galactooligosaccharide (GOS), xylooligosaccharide (XOS), lactosucrose (LACT), soybean oligosaccharides (SOS), Inulin and a combination thereof.

10. The method of claim 1, wherein the composition further comprises a growth factor.

11. The method of claim 1, wherein the composition comprises $1 \times 10 - 1 \times 10^{10}$ cfu/mL or cfu/g of *Faecalibacterium longum* CM04-06, based on the total volume or total weight of the composition.

12. The method of claim 1, wherein the composition comprises $1 \times 10^4 - 1 \times 10^{10}$ cfu/mL or cfu/g of *Faecalibacterium longum* CM04-06, based on the total volume or total weight of the composition.

13. The method of claim 1, wherein the composition is selected from the group consisting of a food composition, a health care composition, a pharmaceutical composition, a beverage composition, a feed composition and a combination thereof.

14. The method of claim 1, wherein the composition is administered orally.

15. The method of claim 1, wherein the administration dosage of the composition is 0.01-5 g/50 kg body weight/day.

16. The method of claim 1, wherein the composition is in a unit dosage form of one tablet, one capsule or one vial, and the mass of the composition in each unit dosage form is of the weight from 0.05 to 5 g.

17. The method of claim 7, wherein the food acceptable or pharmaceutically acceptable carrier is selected from excipient, lubricant, wetting agent, emulsifier, suspension stabilizer, preservative, sweetener and fragrance.

18. The method of claim 1, wherein the composition is of a dosage form selected from the group consisting of powder, pulvis, tablet, sugar coating agent, capsule, granule, suspension, solution, syrup, drop and sublingual tablet.

19. A production method, comprising the following steps:
  (a) cultivating an isolated *Faecalibacterium longum* under anaerobic conditions with a liquid medium at a temperature of 30 to 45° C. and pH of 4.0 to 9.0, thereby obtaining a culture product, wherein the *Faecalibacterium longum* has a sequence of 16s rDNA as set forth in SEQ ID NO: 1;
  (b) isolating *Faecalibacterium longum* bacteria cells from the culture product; and
  (c) mixing the *Faecalibacterium longum* bacteria cells isolated in the step (b) with a food acceptable or pharmaceutically acceptable carrier, thereby obtaining a composition.

20. The production method of claim 18, wherein the *Faecalibacterium longum* is *Faecalibacterium longum* CM04-06 with a deposit number of CGMCC 1.5208.

* * * * *

SEQUENCE LISTING

```
<160> NUMBER OF SEQ ID NOS: 3

<210> SEQ ID NO 1
<211> LENGTH: 1372
<212> TYPE: DNA
<213> ORGANISM: Faecalibacterium longum CM04-06

<400> SEQUENCE: 1
caagtcgaac gagagatgag gagcttgctc ttcagatcga gtggcgaacg ggtgagtaac      60
gcgtgaggaa cctgcctcaa agaggggggac aacagttgga aacgactgct aataccgcat     120
aagcccacgg ctcggcatcg agcagaggga aaaggagtga tccgctttga gatggcctcg     180
cgtccgatta gctggttggt gaggtaacgg cccaccaagg cgacgatcgg tagccggact     240
gagaggttga acggccacat tgggactgag acacggccca gactcctacg ggaggcagca     300
gtggggaata ttgcacaatg ggggaaaccc tgatgcagcg acgccgcgtg gaggaagaag     360
gtcttcggat tgtaaactcc tgttgttgag gaagataatg acggtactca acaaggaagt     420
gacggctaac tacgtgccag cagccgcggt aaaacgtagg tcacaagcgt tgtccggaat     480
tactgggtgt aaagggagcg caggcgggag aacaagttgg aagtgaaatc catgggctca     540
acccatgaac tgctttcaaa actgtttttc ttgagtagtg cagaggtagg cggaattccc     600
ggtgtagcgg tggaatgcgt agatatcggg aggaacacca gtggcgaagg cggcctactg     660
ggcaccaact gacgctgagg ctcgaaagtg tgggtagcaa acaggattag ataccctggt     720
agtccacacc gtaaacgatg attactaggt gttggaggat tgaccccttc agtgccgcag     780
ttaacacaat aagtaatcca cctggggagt acgaccgcaa ggttgaaact caaaggaatt     840 gacggggggcc cgcacaagca gtggagtatg tggtttaatt cgacgcaacg cgaagaacct     900
taccaagtct tgacatccct tgacgaacat agaaatattt tttctcttcg gagcaaggag     960
acaggtggtg catggttgtc gtcagctcgt gtcgtgagat gttgggttaa gtcccgcaac    1020
gagcgcaacc cttatggtca gttactacgc aagaggactc tggccagact gccgttgaca    1080
aaacggagga aggtggggat gacgtcaaat catcatgccc tttatgactt gggctacaca    1140
cgtactacaa tggcgttaaa caaagagaag caagaccgcg aggtggagca aaactcagaa    1200
acaacgtccc agttcggact gcaggctgca actcgcctgc acgaagtcgg aattgctagt    1260
aatcgtggat cagcatgcca cggtgaatac gttcccgggc cttgtacaca ccgcccgtca    1320
caccatgaga gccggggga cccgaagtcg gtagtctaac cgcaaggagg ac             1372

<210> SEQ ID NO 2
<211> LENGTH: 20
<212> TYPE: DNA
<213> ORGANISM: artificial sequence
<220> FEATURE:
<223> OTHER INFORMATION: Primer

<400> SEQUENCE: 2
```

```
agagtttgat catggctcag                                                    20

<210> SEQ ID NO 3
<211> LENGTH: 22
<212> TYPE: DNA
<213> ORGANISM: artificial sequence
<220> FEATURE:
<223> OTHER INFORMATION: primer

<400> SEQUENCE: 3
tagggttacc ttgttacgac tt                                                 22
```